(12) United States Patent
Mailaender et al.

(10) Patent No.: US 12,334,672 B2
(45) Date of Patent: Jun. 17, 2025

(54) PATIENT MONITORING SYSTEM

(71) Applicant: KONINKLIJKE PHILIPS N.V., Eindhoven (NL)

(72) Inventors: Siegfried Mailaender, Dusslingen (DE); Sujit Ranjan Mishra, Darmsheim/ Sindelfingen (DE); Fabian Trogele, Boeblingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 355 days.

(21) Appl. No.: 17/795,079

(22) PCT Filed: Jan. 20, 2021

(86) PCT No.: PCT/EP2021/051093
§ 371 (c)(1),
(2) Date: Jul. 25, 2022

(87) PCT Pub. No.: WO2021/151729
PCT Pub. Date: Aug. 5, 2021

(65) Prior Publication Data
US 2023/0081255 A1    Mar. 16, 2023

(30) Foreign Application Priority Data
Jan. 29, 2020 (EP) .................................. 20154221

(51) Int. Cl.
*H01R 13/52* (2006.01)
(52) U.S. Cl.
CPC .... *H01R 13/5219* (2013.01); *A61B 2562/227* (2013.01)

(58) Field of Classification Search
CPC .................. H01R 13/5219; A61B 2562/227
USPC ........................................................ 439/271
See application file for complete search history.

(56) References Cited

U.S. PATENT DOCUMENTS

| | | | |
|---|---|---|---|
| 7,606,606 B2 * | 10/2009 | Laakkonen | A61B 5/14552 600/336 |
| 7,762,837 B2 | 7/2010 | Kent | |
| 8,384,250 B2 * | 2/2013 | Underwood | G02B 6/3897 700/262 |
| 8,920,329 B2 * | 12/2014 | Knoll | A61B 5/02141 600/485 |
| 10,505,311 B2 * | 12/2019 | Al-Ali | A61B 5/303 |

(Continued)

FOREIGN PATENT DOCUMENTS

| | | |
|---|---|---|
| CN | 1840770 A | 10/2006 |
| WO | 2007143626 A2 | 12/2007 |

(Continued)

OTHER PUBLICATIONS

International Search Report Dated Mar. 24, 2021 For Internation Application No. PCT/EP2021/051093 Filed Jan. 20, 2021.

*Primary Examiner* — Abdullah A Riyami
*Assistant Examiner* — Vladimir Imas

(57) ABSTRACT

A patient monitoring system has a patient monitor and a patient sensor connected to the patient monitor by a measurement cable. An electrical connector between the end of the measurement cable and the patient monitor has a male part with a shroud around a set of pins and a female part with a recess around a set of openings. An annular seal is provided between a surface of the shroud and a surface of the recess.

19 Claims, 3 Drawing Sheets

(56) References Cited

U.S. PATENT DOCUMENTS

| | | | |
|---|---|---|---|
| 10,637,181 B2* | 4/2020 | Al-Ali | A61B 5/303 |
| 10,707,605 B2* | 7/2020 | Kloss | H01R 4/50 |
| 11,095,068 B2* | 8/2021 | Al-Ali | H01R 13/5205 |
| 11,392,449 B2* | 7/2022 | Novak | G11C 16/26 |
| 11,705,666 B2* | 7/2023 | Al-Ali | H01R 13/5205 |
| | | | 439/378 |
| 11,721,939 B2* | 8/2023 | Lund | H01R 13/642 |
| | | | 439/607.17 |
| 2002/0101041 A1 | 8/2002 | Kameyama | |
| 2004/0077203 A1 | 4/2004 | Dewitt | |
| 2009/0197460 A1 | 8/2009 | Kent | |
| 2012/0045912 A1 | 2/2012 | Dai | |
| 2014/0001751 A1 | 1/2014 | Christian | |
| 2016/0084414 A1 | 3/2016 | Groepper | |
| 2019/0058280 A1* | 2/2019 | Al-Ali | A61B 5/303 |
| 2019/0058281 A1 | 2/2019 | Al-Ali | |
| 2019/0067858 A1 | 2/2019 | Kloss | |

FOREIGN PATENT DOCUMENTS

| | | |
|---|---|---|
| WO | 2012003798 A1 | 1/2012 |
| WO | 2019193212 A1 | 10/2019 |

* cited by examiner

PATIENT MONITORING SYSTEM

CROSS-REFERENCE TO PRIOR APPLICATIONS

This application is the U.S. National Phase application under 35 U.S.C. § 371 of International Application No. PCT/EP2021/051093, filed on Jan. 20, 2021, which claims the benefit of European Application No. 20154221.4 filed on Jan. 29, 2020. These applications are hereby incorporated by reference herein.

FIELD OF THE INVENTION

This invention relates to patient monitoring systems, for example for vital signs measurement.

BACKGROUND OF THE INVENTION

A patient monitoring system typically comprises a base unit, known as the patient monitor, and a set of sensors which may be used to monitor one or more physiological parameters of the patient. These sensors connect to the patient monitor by cables.

There may be a set of different sensor types to which the patient monitor may be connected, and they may each have a different type of connector for connection to the patient monitor.

The connectors typically comprise a male pin part and a female socket part, with a push fit coupling. This gives greatest ease of use for connecting and disconnecting the cables.

For in-home and in-hospital use such patient monitoring systems function well. However, when patient monitoring is required in emergency situations, such as outdoors at the scene of an accident, moisture ingress may occur. This can influence the measurements taken as a result of undesired reductions in resistance or even short circuits.

There is a need for a watertight connector, but without sacrificing the ease of use or making the electrical connector unduly complex.

SUMMARY OF THE INVENTION

The invention is defined by the claims.

According to examples in accordance with an aspect of the invention, there is provided a patient monitoring system, comprising:
- a patient monitor;
- a patient sensor;
- a measurement cable coupled to the patient sensor, for removable connection to the patient monitor at an end of the measurement cable; and
- an electrical connector between the end of the cable and the patient monitor, wherein the electrical connector comprises:
  - a male part comprising a set of pins and an annular shroud surrounding the set of pins;
  - a female part comprising a set of pin openings each for receiving a respective pin of the set of pins, and a recess surrounding the set of pin openings for receiving the annular shroud; and
  - an annular seal between a surface of the shroud and a facing surface of the recess.

This patient monitor uses a seal between a shroud of a male connector part and a recess of a female connector part. In this way, a single seal is used which surrounds the connector pins. The seal takes no additional space in that it simply fills a radial space between the shroud and the recess. The invention may be applied as a modified male connector part which can then connect to an existing female connector part, or it may be applied as a modified female connector part which can then connect to an existing male connector part. Thus, an existing patient monitor may be used with updated sensor cables, or else a new patient monitor may be used with existing sensor cables.

The patient monitoring system may then be used in damp or wet situations such as in rescue helicopters, ambulances, military vehicles etc.

The annular seal is for example between an outer surface of the shroud and an inner surface of the recess. This is the radially outermost part of the connector and hence the first point of possible water ingress.

The male part is for example part of the measurement cable and the female part is part of the patient monitor. The patient monitor thus has no protruding pins. Of course, the patient monitor may instead include the male connector part and the measurement cable may have the female connector part.

The annular shroud for example extends at least to the ends of the pins of the set of pins. Thus, it provides protection against damage of the pins as well as providing a surface which can be adapted to provide a seal.

The annular shroud and recess are circular or non-circular, and the male part and the female are for example connectable with only one relative angular orientation. Thus, the term "annular" does not imply a circular shape. Connection with a single orientation ensures the correct connection between the pins and the pin openings.

The annular seal may comprise a set of one or more radially protruding lips which are adapted to compress radially when the male part is received in the female part. The lips are for example biased in a direction opposite to this radial compression such that when compressed they create a seal.

The annular seal is for example a silicone seal or an Ethylene Propylene Diene Monomer, EPDM, seal. A VWQ silicone may for example be used.

For some seal materials, the annular seal may be integrally formed using 2K molding. Thus it may be an integral part of the component to which it is attached. This prevents any risk of detachment and loss of the seal. For other seal materials, seal may be glued, for example behind a locating bezel.

The patient sensor is for example for vital signs measurement. This may for example include ECG monitoring (with various possible leadsets), respiration monitoring, temperature monitoring, pulse oximetry measurement such as FAST (Fourier Artifact Suppression Technology) SpO2, pressure monitoring, and continuous cardiac output (CCO) monitoring.

In a first set of examples, the annular seal is connected to a radially outwardly facing surface of the shroud. Thus, it is provided as a modification to the male connector part, for example a modification to a measurement cable.

In a second set of examples, the annular seal is connected to a radially inwardly facing surface of the recess. Thus, it is provided as a modification to the female connector part, for example a modification to a patient monitor.

The invention also provides a sensor cable for connection to a patient monitor, thereby to form a patient monitoring system as defined above, wherein the sensor cable comprises:
- a patient sensor;

a measurement cable coupled to the patient sensor; and a male connector at an end of the measurement cable comprising a set of pins, an annular shroud surrounding the set of pins and an annular seal connected to a surface of the annular shroud; or a female connector at an end of the measurement cable comprising a set of pin openings, a recess surrounding the set of pin openings and an annular seal connected to a surface of the recess.

This is the modified patient sensor cable.

The invention also provides a patient monitor for connection to a patient sensor by means of a measurement cable, thereby to form a patient monitoring system as defined above, wherein the patient monitor comprises:

a male connector comprising a set of pins, an annular shroud surrounding the set of pins and an annular seal connected to a surface of the annular shroud; or a female connector comprising a set of pin openings, a recess surrounding the set of pin openings and an annular seal connected to a surface of the recess.

This is the modified patient monitor.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
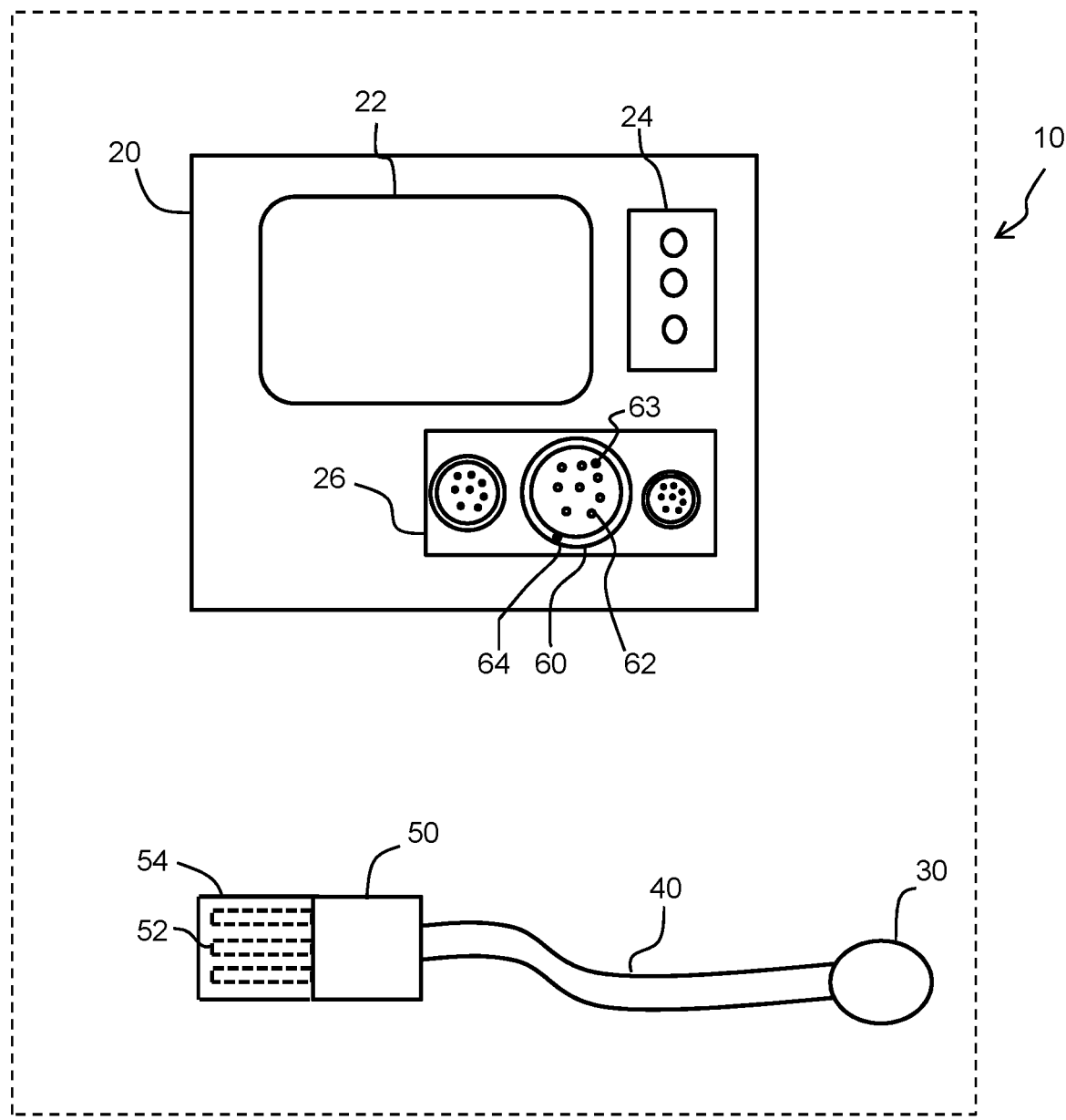
FIG. 1 shows a patient monitoring system, comprising a patient monitor, a patient sensor and a measurement cable.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

A patient monitoring system has a patient monitor and a patient sensor connected to the patient monitor by a measurement cable. An electrical connector between an end of the measurement cable and the patient monitor has a male part with a shroud around a set of pins and a female part with a recess around a set of openings. An annular seal is provided between a surface of the shroud and a surface of the recess.

FIG. 1 shows a patient monitoring system 10, comprising a patient monitor 20, a patient sensor 30 and a measurement cable 40 coupled to the patient sensor, for removable connection to the patient monitor at an end of the cable. The patient sensor is for example for vital signs measurement. This may for example include ECG monitoring, respiration monitoring, temperature monitoring and others. In the context of the present application the patient sensor can be also a cable trunk to which a sensing element of the patient sensor can be coupled to. For example, the patient sensor (30) can be an ECG trunk, to which a variety of ECG leads can be connected to.

An electrical connector is provided between the end of the measurement cable 40 and the patient monitor 20.

The electrical connector comprises a male part 50 and a female part 60.

In the example shown, the measurement cable 40 is terminated with the male part and the patient monitor has the female part. However, the electrical connector could be the other way around.

The male part comprises a set of pins 52 and an annular shroud 54 surrounding the set of pins. The female part 60 comprises a set of pin openings 62 extending into a connector body 63, each pin opening 62 for receiving a respective pin 52 of the set of pins, and a recess 64 surrounding the set of pin openings for receiving the annular shroud 54.

The invention provides an annular seal between a surface of the shroud 54 and a surface of the recess 64.

This patient monitoring system thus uses a seal between a shroud of a male connector part and a recess of a female connector part. In this way, a single seal is used which surrounds the connector pins. This enables the patient monitoring system to be used in damp or wet situations such as in rescue helicopters, ambulances, military vehicles etc.

Figure 2:
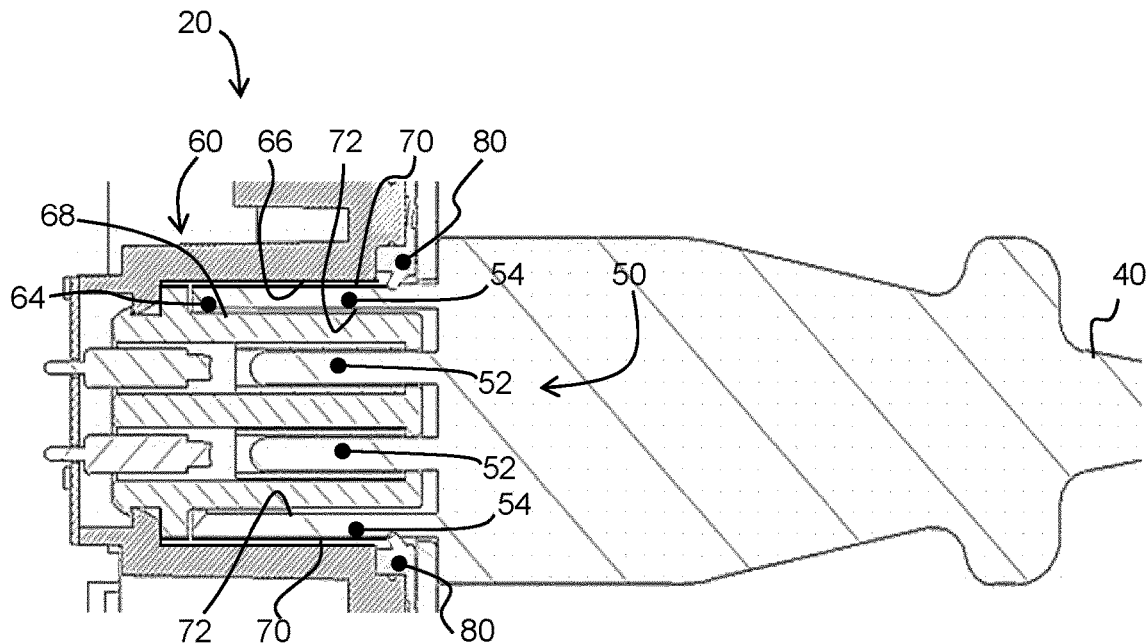
FIG. 2 shows a first example of an electrical connector for used in the system of FIG. 1.

FIG. 2 shows a first example of the electrical connector. In this example, the male part 50 is part of, and at the end of, the measurement cable 40 and the female part 60 is part of the patient monitor 20.

The annular shroud 54 extends beyond the ends of the pins 52 so protects the pins from damage as well as providing an alignment feature between the male and female parts of the connector.

The annular shroud comprises a closed ring which may be circular or non-circular. It has a radially outwardly facing outermost lateral surface 70 and a radially inwardly facing innermost lateral surface 72.

The recess 64 has a corresponding shape. The recess 64 has an outermost inwardly facing lateral surface 66 and an innermost outwardly facing lateral surface 68.

In the example shown, the annular seal 80 extends between the radially outwardly facing lateral surface 70 of the shroud and the radially inwardly facing lateral surface 66 of the recess 64. Thus, the annular seal is positioned around the outside of the shroud.

The seal could however be positioned between the innermost outwardly facing lateral surface 68 of the recess and the radially inwardly facing lateral surface 72 of the shroud. Sealing this passage similarly provides protection of the electrical contacts from water ingress. However, the seal in FIG. 2 is positioned at the first possible point of water ingress.

In the example of FIG. 2, the annular seal is attached to the outermost inwardly facing lateral surface 66 of the recess, and hence is fixed to the patient monitor. This means a conventional sensor cable may be used. Thus, a modified patient monitor may be used with standard sensor cables and then provide protection against water ingress. The invention also provides such a modified patient monitor.

The modified patient monitor may either have:
- a female connector comprising a set of pin openings, and a recess surrounding the set of pin openings, and an annular seal connected to a surface of the recess (as shown in FIG. 2); or
- a male connector comprising a set of pins, an annular shroud surrounding the set of pins and an annular seal connected to a surface of the annular shroud (hence the opposite polarity of the connector).

The annular seal 80 is shown in FIG. 2 as having a radially protruding lip. The lip preferably compresses radially when the male part is received in the female part, thus providing a seal. The lip for example faces in the direction of the bottom of the recess so that it is bent downwardly upon insertion of the male part of the connector.

Figure 3:
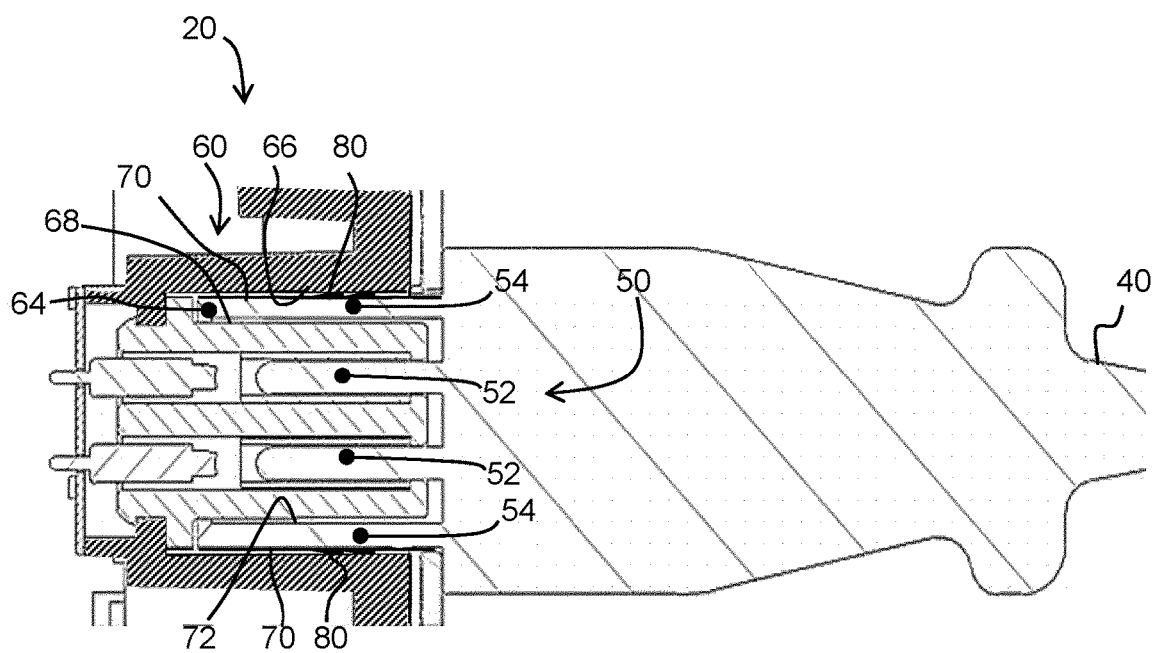
FIG. 3 shows a second example of an electrical connector for used in the system of FIG. 1.

FIG. 3 shows a second example of the electrical connector. The male part 50 is again part of the measurement cable 40 and the female part is part 60 of the patient monitor 20.

The same design is shown as in FIG. 2 but with a different seal design. The seal again extends between the radially outwardly facing lateral surface 70 of the shroud and the outermost inwardly facing lateral surface 66 of the recess 64.

In the example of FIG. 3, the annular seal is attached to the radially outwardly facing lateral surface 70 and hence is fixed to the male connector part at the end of the sensor cable. This means a conventional patient monitor may be used. Thus, a modified sensor cable may be used with a standard patient monitor to provide protection against water ingress. The invention also provides such a modified sensor cable having a patient sensor, a measurement cable coupled to the patient sensor and a connector at an end of the measurement cable. The connector may comprise:
- a male connector comprising a set of pins, an annular shroud surrounding the set of pins and an annular seal connected to a surface of the annular shroud; or
- a female connector comprising a set of pin openings, a recess surrounding the set of pin openings and an annular seal connected to a surface of the recess.

The annular seal is shown in FIG. 3 as having a pair of radially protruding lips, i.e. two annular seals in series. The lips again compress radially when the male part is received in the female part, thus providing a seal. The lips for example again face in the direction of the bottom of the recess so that they are bent downwardly upon insertion of the male part of the connector.

In all examples, the annular seal may be a silicone seal or an Ethylene Propylene Diene Monomer, EPDM, seal. A VMQ silicone seal may for example be used. Depending on the type of seal material, the annular seal may be integrally formed using 2K molding. Thus it may be an integral part of the component to which it is attached. This prevents any risk of detachment and loss of the seal.

The annular seal for example does not need to sit in a recess but is formed integrally with the surface from which it projects. The seal may instead be glued to the part to which it is to be connected. It may for example be located by a bezel, to which it is glued or welded.

Figure 4:
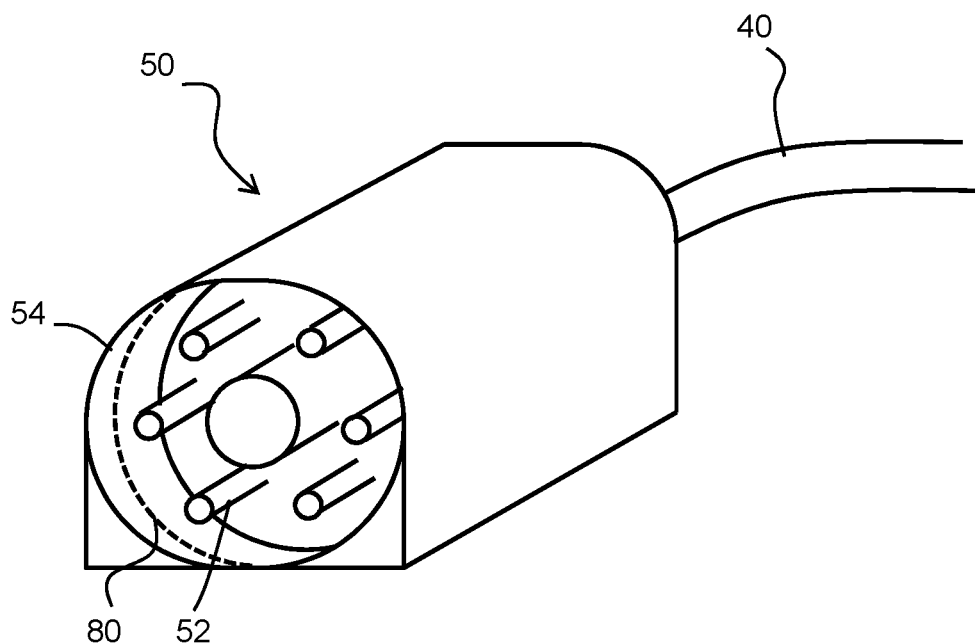
FIG. 4 shows an example of a male connector part of a sensor cable, more clearly.

FIG. 4 shows an example of a male connector part 50, in this example shown at the end of a measurement cable 40, more clearly. The seal 80 is on the inner surface of the shroud 54, surrounding the pins 52. In this example, the connector part is circular, but the overall shape of the male connector 50 is non-circular so that it has only one possible angular orientation with which it can fit to the female connector part.

Figure 5:
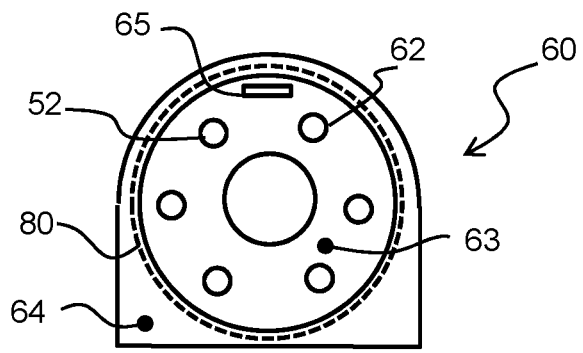
FIG. 5 shows an example of a female connector part of a patient monitor, more clearly.

FIG. 5 shows an example of a female connector part, for example for the patient monitor, for mating with the male connector part of FIG. 4. It shows the seal 80 around the projecting body 63. The recess 64 has a non-constant width so that it can accommodate the outer shape of the male part. A locking feature is shown schematically as 65, which may click the male connector in place to prevent accidental decoupling of the connector.

The seal 80 will typically be in only one of the male connector part and the female connector part, but there could be seals in both, for example with the seal of the female connector part at a deeper location (i.e. further towards the bottom of the recess 64) than the seal of the male connector part, so they do not interfere with each other.

Figure 6:
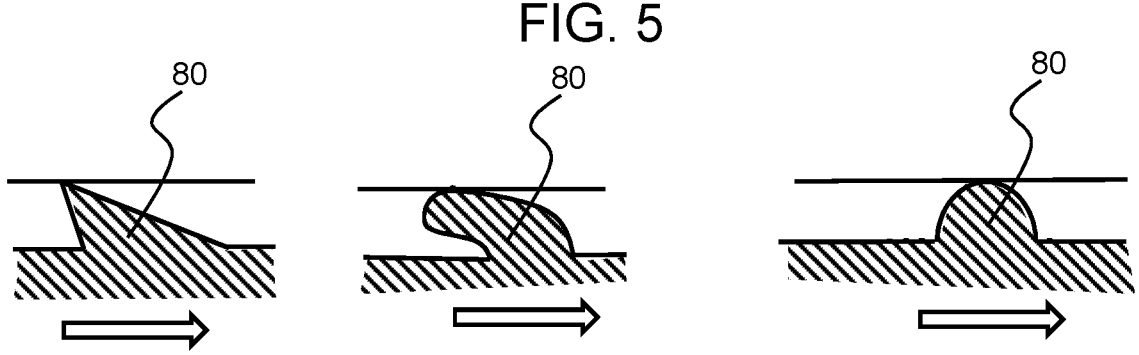
FIG. 6 shows some seal designs.

FIG. 6 shows three examples of possible seal shapes and show the seal as an integral part of one of the two connector parts. The arrows shows the direction of movement of the connector part carrying the seal assuming it is part of the measurement cable, but equally the seal may be static and the other connector part may move.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

The mere fact that certain measures are recited in mutually different dependent claims does not indicate that a combination of these measures cannot be used to advantage.

If the term "adapted to" is used in the claims or description, it is noted the term "adapted to" is intended to be equivalent to the term "configured to".

Any reference signs in the claims should not be construed as limiting the scope.

The invention claimed is:

1. A patient monitoring system, comprising:
   a patient monitor;
   a patient sensor;
   a measurement cable coupled to the patient sensor, for removable connection to the patient monitor at an end of the measurement cable; and
   an electrical connector between the end of the measurement cable and the patient monitor, wherein the electrical connector comprises:
      a male part comprising a set of pins and an annular shroud surrounding the set of pins;
      a female part comprising a set of pin openings each for receiving a respective pin of the set of pins, and a recess surrounding the set of pin openings for receiving the annular shroud; and
      an annular seal between a surface of the shroud and a facing surface of the recess, wherein the annular seal is between an outer surface of the shroud and an inner surface of the recess.

2. The patient monitoring system as claimed in claim 1, wherein the male part is part of the measurement cable and the female part is part of the patient monitor.

3. The patient monitoring system as claimed in claim 1, wherein the annular shroud extends at least to the ends of the pins of the set of pins.

4. The patient monitoring system as claimed in claim 1, wherein the annular shroud and recess are circular or non-circular, wherein the male part and the female part are connectable with only one relative angular orientation.

5. The patient monitoring system as claimed in claim 1, wherein the annular seal comprises a set of one or more radially protruding lips which are adapted to compress radially when the male part is received in the female part.

6. The patient monitoring system as claimed in claim 1, wherein the annular seal is a silicone seal.

7. The patient monitoring system as claimed in claim 1, wherein the annular seal is an Ethylene Propylene Diene Monomer, EPDM, seal.

8. The patient monitoring system as claimed in claim 6, wherein the annular seal is integrally formed using 2K molding.

9. The patient monitoring system as claimed in claim 1, wherein the patient sensor is for vital signs measurement.

10. The patient monitoring system as claimed in claim 1, wherein the annular seal is connected to a radially outwardly facing surface of the shroud.

11. The patient monitoring system as claimed in claim 1, wherein the annular seal is connected to a radially inwardly facing surface of the recess.

12. A sensor cable system for connection to a patient monitor, wherein the sensor cable system comprises:
 a patient sensor;
 a measurement cable coupled to the patient sensor;
 a male connector at an end of the measurement cable comprising a set of pins, and an annular shroud surrounding the set of pins;
 a female connector at an end of the measurement cable comprising a set of pin openings, and a recess surrounding the set of pin openings; and
 an annular seal, wherein the annular seal is between an outer surface of the shroud and an inner surface of the recess.

13. A patient monitor for connection to a patient sensor by means of a measurement cable, wherein the patient monitor comprises:
 a male connector comprising a set of pins, and an annular shroud surrounding the set of pins;
 a female connector comprising a set of pin openings, and a recess surrounding the set of pin openings; and
 an annular seal, wherein the annular seal is between an outer surface of the shroud and an inner surface of the recess.

14. The sensor cable as claimed in claim 12, wherein the annular shroud extends at least to the ends of the pins of the set of pins.

15. The sensor cable as claimed in claim 12, wherein the annular seal is connected to a radially outwardly facing surface of the shroud.

16. The sensor cable as claimed in claim 12, wherein the annular seal is connected to a radially inwardly facing surface of the recess.

17. The patient monitor as claimed in claim 13, wherein the annular shroud extends at least to the ends of the pins of the set of pins.

18. The patient monitor as claimed in claim 13, wherein the annular seal is connected to a radially outwardly facing surface of the shroud.

19. The patient monitor as claimed in claim 13, wherein the annular seal is connected to a radially inwardly facing surface of the recess.

* * * * *